(12) United States Patent
Edwards et al.

(10) Patent No.: US 9,218,664 B2
(45) Date of Patent: *Dec. 22, 2015

(54) APPARATUS AND METHOD FOR IMAGE GUIDED ACCURACY VERIFICATION

(75) Inventors: Jerome R. Edwards, Nashville, TN (US); Evan Austill, Jr., Nashville, TN (US); Torsten M. Lyon, Golden, CO (US); Troy L. Holsing, Nashville, TN (US)

(73) Assignee: Veran Medical Technologies, Inc., St. Louis, MO (US)

( * ) Notice: Subject to any disclaimer, the term of this patent is extended or adjusted under 35 U.S.C. 154(b) by 914 days.

This patent is subject to a terminal disclaimer.

(21) Appl. No.: 13/103,674

(22) Filed: May 9, 2011

(65) Prior Publication Data

US 2011/0208044 A1 Aug. 25, 2011

Related U.S. Application Data

(60) Division of application No. 12/724,689, filed on Mar. 16, 2010, now Pat. No. 7,962,193, which is a continuation of application No. 11/224,028, filed on Sep. 13, 2005, now abandoned.

(51) Int. Cl.
*A61B 5/05* (2006.01)
*G06T 7/00* (2006.01)
(Continued)

(52) U.S. Cl.
CPC .............. *G06T 7/0028* (2013.01); *G06T 7/0038* (2013.01); *G06T 7/2033* (2013.01); *A61B 5/11* (2013.01); *A61B 6/00* (2013.01); *A61B 6/547* (2013.01); *A61B 2576/00* (2013.01)

(58) Field of Classification Search
CPC ......... A61B 2576/00; A61B 6/00; A61B 5/11

USPC .................................................. 600/407–480
See application file for complete search history.

(56) References Cited

U.S. PATENT DOCUMENTS 3,788,324 A 1/1974 Lim
4,421,106 A 12/1983 Uehara
(Continued)

FOREIGN PATENT DOCUMENTS

DE 19751761 10/1998
DE 19725137 1/1999
(Continued)

OTHER PUBLICATIONS

Medical Industry Today, "New Navigational Aid Could Improve Hip Replacement Outcomes" Jul. 11, 1997.
(Continued)

*Primary Examiner* — Baisakhi Roy
*Assistant Examiner* — Vani Gupta
(74) *Attorney, Agent, or Firm* — Bryan Cave LLP

(57) ABSTRACT

A method includes receiving during a first time interval image data associated with an image of a dynamic body. The image data includes an indication of the positions of a first marker and a second marker on a garment coupled to the dynamic body. The first marker and second marker are each coupled to the garment at a first and second locations, respectively. A distance is determined between the position of the first marker and the second marker. During a second time interval after the first time interval, data associated with a position of a first and second localization element that are each coupled to the garment is received. A distance between the first and second localization elements is determined. A difference is calculated between the distance between the first marker and the second marker and the distance between the first localization element and the second localization element.

26 Claims, 7 Drawing Sheets

(51) Int. Cl.
  *G06T 7/20*  (2006.01)
  *A61B 5/11*  (2006.01)
  *A61B 6/00*  (2006.01)

(56) References Cited

U.S. PATENT DOCUMENTS

| | | |
|---|---|---|
| 4,583,538 A | 4/1986 | Onik et al. |
| 5,053,042 A | 10/1991 | Bidwell |
| 5,081,997 A | 1/1992 | Bosley et al. |
| 5,158,088 A | 10/1992 | Nelson et al. |
| 5,186,174 A | 2/1993 | Schlondorff et al. |
| 5,238,004 A | 8/1993 | Sahatjian et al. |
| 5,251,165 A | 10/1993 | James, III |
| 5,251,635 A | 10/1993 | Dumoulin et al. |
| 5,265,610 A | 11/1993 | Darrowm et al. |
| 5,295,493 A | 3/1994 | Radisch |
| 5,348,011 A | 9/1994 | Nessaiver |
| 5,377,678 A | 1/1995 | Dumoulin et al. |
| 5,391,199 A | 2/1995 | Ben-Haim |
| 5,437,292 A | 8/1995 | Kipshidze et al. |
| 5,483,691 A | 1/1996 | Heck et al. |
| 5,483,961 A | 1/1996 | Kelly et al. |
| 5,577,502 A | 11/1996 | Darrow et al. |
| 5,581,183 A | 12/1996 | Lindstedt et al. |
| 5,644,612 A | 7/1997 | Moorman et al. |
| 5,671,739 A | 9/1997 | Darrow et al. |
| 5,718,241 A | 2/1998 | Ben-Haim et al. |
| 5,730,129 A | 3/1998 | Darrow et al. |
| 5,740,808 A | 4/1998 | Panescu et al. |
| 5,765,561 A | 6/1998 | Chen et al. |
| 5,769,789 A | 6/1998 | Wang |
| 5,769,861 A | 6/1998 | Vilsmeier |
| 5,771,306 A | 6/1998 | Stork et al. |
| 5,787,886 A | 8/1998 | Kelly et al. |
| 5,803,089 A | 9/1998 | Ferre et al. |
| 5,814,022 A | 9/1998 | Antanavich et al. |
| 5,814,066 A | 9/1998 | Spotnitz |
| 5,833,608 A | 11/1998 | Acker |
| 5,840,025 A | 11/1998 | Ben-Haim |
| 5,868,673 A | 2/1999 | Vesely |
| 5,928,248 A | 7/1999 | Acker |
| 5,951,461 A | 9/1999 | Nyo |
| 5,978,696 A | 11/1999 | Vomlehn et al. |
| 6,016,439 A | 1/2000 | Acker |
| 6,019,724 A | 2/2000 | Gronningsaeter et al. |
| 6,026,173 A | 2/2000 | Svenson et al. |
| 6,078,175 A | 6/2000 | Foo |
| 6,122,538 A | 9/2000 | Sliwa, Jr. et al. |
| 6,122,541 A | 9/2000 | Cosman et al. |
| 6,132,396 A | 10/2000 | Antanavich et al. |
| 6,139,508 A | 10/2000 | Kilcoyne et al. |
| 6,144,875 A | 11/2000 | Schweikard et al. |
| 6,167,296 A | 12/2000 | Shahidi |
| 6,173,201 B1 | 1/2001 | Front |
| 6,188,355 B1 | 2/2001 | Gilboa |
| 6,198,959 B1 | 3/2001 | Wang |
| 6,201,987 B1 | 3/2001 | Dumoulin |
| 6,226,543 B1 | 5/2001 | Gilboa et al. |
| 6,226,548 B1 | 5/2001 | Foley et al. |
| 6,233,476 B1 | 5/2001 | Strommer et al. |
| 6,235,038 B1 | 5/2001 | Hunter et al. |
| 6,236,875 B1 | 5/2001 | Bucholz et al. |
| 6,246,896 B1 | 6/2001 | Dumoulin et al. |
| 6,246,898 B1 | 6/2001 | Vesely et al. |
| 6,253,770 B1 | 7/2001 | Acker et al. |
| 6,254,550 B1 | 7/2001 | McNamara et al. |
| 6,267,769 B1 | 7/2001 | Truwit |
| 6,275,560 B1 | 8/2001 | Blake et al. |
| 6,282,442 B1 | 8/2001 | DeStefano et al. |
| 6,285,902 B1 | 9/2001 | Kienzle, III et al. |
| 6,298,259 B1 | 10/2001 | Kucharczyk et al. |
| 6,314,310 B1 | 11/2001 | Ben-Haim et al. |
| 6,314,311 B1 | 11/2001 | Williams et al. |
| 6,314,312 B1 | 11/2001 | Wessels et al. |
| 6,317,616 B1 | 11/2001 | Glossop |
| 6,317,619 B1 | 11/2001 | Boernert et al. |
| 6,330,356 B1 | 12/2001 | Sundareswaran et al. |
| 6,332,089 B1 | 12/2001 | Acker et al. |
| 6,332,891 B1 | 12/2001 | Himes |
| 6,335,617 B1 | 1/2002 | Osadchy et al. |
| 6,335,623 B1 | 1/2002 | Damadian et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,351,573 B1 | 2/2002 | Schneider |
| 6,351,659 B1 | 2/2002 | Vilsmeier |
| 6,361,759 B1 | 3/2002 | Frayne et al. |
| 6,362,821 B1 | 3/2002 | Gibson et al. |
| 6,368,331 B1 | 4/2002 | Front et al. |
| 6,369,571 B1 | 4/2002 | Damadian et al. |
| 6,373,998 B2 | 4/2002 | Thirion et al. |
| 6,379,302 B1 | 4/2002 | Kessman et al. |
| 6,380,732 B1 | 4/2002 | Gilboa |
| 6,381,485 B1 | 4/2002 | Hunter et al. |
| 6,402,762 B2 | 6/2002 | Hunter et al. |
| 6,418,238 B1 | 7/2002 | Shiratani et al. |
| 6,421,551 B1 | 7/2002 | Kuth et al. |
| 6,424,856 B1 | 7/2002 | Vilsmeier et al. |
| 6,425,865 B1 | 7/2002 | Salcudean et al. |
| 6,430,430 B1 | 8/2002 | Gosche |
| 6,434,415 B1 | 8/2002 | Foley et al. |
| 6,434,507 B1 | 8/2002 | Clayton et al. |
| 6,437,571 B1 | 8/2002 | Danby et al. |
| 6,442,417 B1 | 8/2002 | Shahidi et al. |
| 6,445,186 B1 | 9/2002 | Damadian et al. |
| 6,445,943 B1 | 9/2002 | Ferre et al. |
| 6,455,182 B1 | 9/2002 | Silver |
| 6,461,372 B1 | 10/2002 | Jensen et al. |
| 6,468,265 B1 | 10/2002 | Evans et al. |
| 6,469,508 B1 | 10/2002 | Damadian et al. |
| 6,470,066 B2 | 10/2002 | Takagi et al. |
| 6,470,207 B1 | 10/2002 | Simon et al. |
| 6,473,635 B1 | 10/2002 | Rashe |
| 6,477,400 B1 | 11/2002 | Barrick |
| 6,478,793 B1 | 11/2002 | Cosman et al. |
| 6,478,802 B2 | 11/2002 | Kienzle, III et al. |
| 6,483,948 B1 | 11/2002 | Spink et al. |
| 6,484,049 B1 | 11/2002 | Seeley et al. |
| 6,485,413 B1 | 11/2002 | Boppart et al. |
| D466,609 S | 12/2002 | Glossop |
| D466,610 S | 12/2002 | Ashton et al. |
| 6,490,467 B1 | 12/2002 | Bucholz et al. |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,491,702 B2 | 12/2002 | Heilbrun et al. |
| 6,493,574 B1 | 12/2002 | Ehnholm et al. |
| 6,496,007 B1 | 12/2002 | Damadian et al. |
| 6,501,981 B1 | 12/2002 | Schweikard et al. |
| 6,504,893 B1 | 1/2003 | Flohr et al. |
| 6,504,894 B2 | 1/2003 | Pan et al. |
| 6,516,213 B1 | 2/2003 | Nevo |
| 6,517,485 B2 | 2/2003 | Torp et al. |
| 6,527,443 B1 | 3/2003 | Vilsmeier et al. |
| 6,535,756 B1 | 3/2003 | Simon et al. |
| 6,538,634 B1 | 3/2003 | Chui et al. |
| 6,539,127 B1 | 3/2003 | Roche et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,562,059 B2 | 5/2003 | Edwards et al. |
| 6,567,687 B2 | 5/2003 | Front et al. |
| 6,574,498 B1 | 6/2003 | Gilboa |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,593,884 B1 | 7/2003 | Gilboa |
| 6,606,513 B2 | 8/2003 | Lardo et al. |
| 6,609,022 B2 | 8/2003 | Vilsmeier et al. |
| 6,615,155 B2 | 9/2003 | Gilboa |
| 6,636,757 B1 | 10/2003 | Jascob et al. |
| 6,650,924 B2 | 11/2003 | Kuth et al. |

(56) References Cited

U.S. PATENT DOCUMENTS

| | | |
|---|---|---|
| 6,666,579 B2 | 12/2003 | Jensen |
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,702,780 B1 | 3/2004 | Gilboa |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,725,080 B2 | 4/2004 | Melkent et al. |
| 6,738,656 B1 | 5/2004 | Ferre et al. |
| 6,772,002 B2 | 8/2004 | Schmidt et al. |
| 6,774,624 B2 | 8/2004 | Anderson et al. |
| 6,782,287 B2 | 8/2004 | Grzeszczuk et al. |
| 6,796,988 B2 | 9/2004 | Melkent et al. |
| 6,799,569 B2 | 10/2004 | Danielsson et al. |
| 6,823,207 B1 | 11/2004 | Jensen et al. |
| 6,826,423 B1 | 11/2004 | Hardy et al. |
| 6,833,814 B2 | 12/2004 | Gilboa |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,898,303 B2 | 5/2005 | Armato, III et al. |
| 6,899,672 B2 | 5/2005 | Chin et al. |
| 6,907,281 B2 | 6/2005 | Grzeszczuk |
| 6,920,347 B2 | 7/2005 | Simon et al. |
| 6,925,200 B2 | 8/2005 | Wood et al. |
| 6,934,575 B2 | 8/2005 | Ferre et al. |
| 6,947,788 B2 | 9/2005 | Gilboa |
| 6,968,224 B2 | 11/2005 | Kessman et al. |
| 6,978,166 B2 | 12/2005 | Foley et al. |
| 6,992,477 B2 | 1/2006 | Govari |
| 6,996,430 B1 | 2/2006 | Gilboa |
| 7,015,859 B2 | 3/2006 | Anderson |
| 7,015,907 B2 | 3/2006 | Tek et al. |
| 7,035,683 B2 | 4/2006 | Guendel |
| 7,050,845 B2 | 5/2006 | Vilsmeier |
| 7,115,100 B2 | 10/2006 | McRury et al. |
| 7,130,700 B2 | 10/2006 | Gardeski et al. |
| 7,139,601 B2 | 11/2006 | Bucholz et al. |
| 7,153,297 B2 | 12/2006 | Peterson |
| 7,171,257 B2 | 1/2007 | Thomson |
| 7,174,201 B2 | 2/2007 | Govari et al. |
| 7,233,820 B2 | 6/2007 | Gilboa |
| 7,260,426 B2 | 8/2007 | Schweikard et al. |
| 7,300,428 B2 | 11/2007 | Ingenito |
| 7,339,587 B2 | 3/2008 | Kropfeld |
| 7,357,807 B2 | 4/2008 | Donohoe et al. |
| 7,366,562 B2 | 4/2008 | Dukesherer et al. |
| 7,371,067 B2 | 5/2008 | Anderson |
| 7,398,116 B2 | 7/2008 | Edwards |
| 7,481,805 B2 | 1/2009 | Magnusson |
| 7,505,806 B2 | 3/2009 | Masutani et al. |
| 7,555,330 B2 | 6/2009 | Gilboa |
| 7,594,925 B2 | 9/2009 | Danek |
| 7,599,730 B2 | 10/2009 | Hunter et al. |
| 7,641,609 B2 | 1/2010 | Ohnishi |
| 7,659,912 B2 | 2/2010 | Akimoto |
| 7,697,972 B2 | 4/2010 | Verard et al. |
| 7,756,563 B2 | 7/2010 | Higgins |
| 7,889,905 B2 | 2/2011 | Higgins |
| 7,901,348 B2 | 3/2011 | Soper |
| 7,920,909 B2 * | 4/2011 | Lyon et al. ............... 600/407 |
| 7,962,193 B2 * | 6/2011 | Edwards et al. .......... 600/407 |
| 7,969,143 B2 | 6/2011 | Gilboa |
| 7,985,187 B2 | 7/2011 | Wibowo |
| 7,998,062 B2 | 8/2011 | Gilboa |
| 8,016,749 B2 | 9/2011 | Clerc |
| 8,046,052 B2 | 10/2011 | Verard et al. |
| 8,049,777 B2 | 11/2011 | Akimoto |
| 8,064,669 B2 | 11/2011 | Higgins |
| 8,096,957 B2 | 1/2012 | Conquergood et al. |
| 8,102,416 B2 | 1/2012 | Ito |
| 8,150,138 B2 | 4/2012 | Ohnishi |
| 8,150,495 B2 | 4/2012 | Edwards et al. |
| 8,202,213 B2 | 6/2012 | Ito |
| 8,214,015 B2 | 7/2012 | Macaulay et al. |
| 8,218,846 B2 | 7/2012 | Trumer |
| 8,218,847 B2 | 7/2012 | Averbuch |
| 8,219,179 B2 | 7/2012 | Ganatra |
| 8,317,149 B2 | 11/2012 | Greenburg |
| 8,317,726 B2 | 11/2012 | Timberlake et al. |
| 8,382,662 B2 | 2/2013 | Soper |
| 8,428,328 B2 | 4/2013 | Averbuch |
| 8,468,003 B2 | 6/2013 | Gibbs |
| 8,473,032 B2 | 6/2013 | Averbuch |
| 8,483,801 B2 | 7/2013 | Edwards |
| 8,494,246 B2 | 7/2013 | Trumer |
| 8,494,612 B2 | 7/2013 | Vetter |
| 8,611,983 B2 | 12/2013 | Glossop |
| 8,611,984 B2 | 12/2013 | Greenburg |
| 8,632,461 B2 | 1/2014 | Glossop |
| 8,672,836 B2 | 3/2014 | Higgins |
| 8,675,935 B2 | 3/2014 | Higgins |
| 8,696,548 B2 | 4/2014 | Gilboa |
| 8,696,685 B2 | 4/2014 | Gilboa |
| 8,700,132 B2 | 4/2014 | Ganatra |
| 2001/0007918 A1 | 7/2001 | Vilsmeier et al. |
| 2001/0025142 A1 | 9/2001 | Wessels et al. |
| 2001/0029333 A1 | 10/2001 | Shahidi |
| 2001/0031919 A1 | 10/2001 | Strommer et al. |
| 2001/0031985 A1 | 10/2001 | Gilboa et al. |
| 2001/0036245 A1 | 11/2001 | Kienzle et al. |
| 2001/0041835 A1 | 11/2001 | Front et al. |
| 2002/0044631 A1 | 4/2002 | Graumann et al. |
| 2002/0049375 A1 | 4/2002 | Strommer et al. |
| 2002/0049378 A1 | 4/2002 | Grzeszczuk et al. |
| 2002/0070970 A1 * | 6/2002 | Wood et al. ............... 345/766 |
| 2002/0075994 A1 | 6/2002 | Shahidi et al. |
| 2002/0077543 A1 | 6/2002 | Grzeszczuk et al. |
| 2002/0077544 A1 | 6/2002 | Shahidi |
| 2002/0082492 A1 | 6/2002 | Grzeszczuk |
| 2002/0085681 A1 | 7/2002 | Jensen |
| 2002/0115931 A1 * | 8/2002 | Strauss et al. ............. 600/420 |
| 2002/0143317 A1 | 10/2002 | Glossop |
| 2002/0161295 A1 | 10/2002 | Edwards et al. |
| 2003/0000535 A1 | 1/2003 | Galloway, Jr. et al. |
| 2003/0004411 A1 | 1/2003 | Govari et al. |
| 2003/0016852 A1 | 1/2003 | Kaufman et al. |
| 2003/0018251 A1 | 1/2003 | Solomon |
| 2003/0023161 A1 | 1/2003 | Govari et al. |
| 2003/0028091 A1 | 2/2003 | Simon et al. |
| 2003/0029464 A1 | 2/2003 | Chen et al. |
| 2003/0032878 A1 | 2/2003 | Shahidi |
| 2003/0040667 A1 | 2/2003 | Feussner et al. |
| 2003/0051733 A1 | 3/2003 | Kotmel et al. |
| 2003/0074011 A1 | 4/2003 | Gilboa et al. |
| 2003/0088179 A1 | 5/2003 | Seeley et al. |
| 2003/0125622 A1 | 7/2003 | Schweikard et al. |
| 2003/0130576 A1 | 7/2003 | Seeley et al. |
| 2003/0139663 A1 | 7/2003 | Graumann |
| 2003/0199785 A1 | 10/2003 | Hibner et al. |
| 2003/0208116 A1 | 11/2003 | Liang et al. |
| 2003/0208122 A1 | 11/2003 | Melkent et al. |
| 2003/0216631 A1 | 11/2003 | Bloch et al. |
| 2003/0220557 A1 | 11/2003 | Cleary et al. |
| 2004/0006268 A1 | 1/2004 | Gilboa et al. |
| 2004/0034300 A1 | 2/2004 | Verard et al. |
| 2004/0049121 A1 | 3/2004 | Yaron |
| 2004/0076259 A1 | 4/2004 | Jensen et al. |
| 2004/0091143 A1 | 5/2004 | Hu |
| 2004/0092815 A1 | 5/2004 | Schweikard et al. |
| 2004/0097805 A1 | 5/2004 | Verard et al. |
| 2004/0097806 A1 | 5/2004 | Hunter et al. |
| 2004/0116803 A1 | 6/2004 | Jacob et al. |
| 2004/0122311 A1 | 6/2004 | Cosman |
| 2004/0138548 A1 | 7/2004 | Strommer et al. |
| 2004/0152970 A1 | 8/2004 | Hunter et al. |
| 2004/0152974 A1 | 8/2004 | Solomon |
| 2004/0167393 A1 | 8/2004 | Solar et al. |

(56) References Cited

U.S. PATENT DOCUMENTS

| | | |
|---|---|---|
| 2004/0193042 A1 | 9/2004 | Scampini et al. |
| 2004/0210125 A1 | 10/2004 | Chen et al. |
| 2004/0249267 A1 | 12/2004 | Gilboa |
| 2005/0010099 A1 | 1/2005 | Raabe et al. |
| 2005/0020900 A1 | 1/2005 | Yngvesson |
| 2005/0027186 A1 | 2/2005 | Chen et al. |
| 2005/0033149 A1 | 2/2005 | Strommer et al. |
| 2005/0038337 A1 | 2/2005 | Edwards |
| 2005/0065433 A1 | 3/2005 | Anderson |
| 2005/0085718 A1 | 4/2005 | Shahidi |
| 2005/0085793 A1 | 4/2005 | Glossop |
| 2005/0107679 A1 | 5/2005 | Geiger et al. |
| 2005/0107688 A1 | 5/2005 | Srommer |
| 2005/0113809 A1 | 5/2005 | Melkent et al. |
| 2005/0137661 A1 | 6/2005 | Sra |
| 2005/0143651 A1 | 6/2005 | Verard et al. |
| 2005/0169510 A1 | 8/2005 | Zuhars et al. |
| 2005/0182295 A1 | 8/2005 | Soper et al. |
| 2005/0182319 A1 | 8/2005 | Glossop |
| 2005/0187482 A1 | 8/2005 | O'Brien et al. |
| 2005/0197568 A1 | 9/2005 | Vass et al. |
| 2005/0203383 A1 | 9/2005 | Moctezuma de la Barrera et al. |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1* | 1/2006 | Saracen ..................... 600/414 |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0063998 A1 | 3/2006 | Von Jako et al. |
| 2006/0064006 A1 | 3/2006 | Strommer et al. |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0142798 A1 | 6/2006 | Holman et al. |
| 2006/0173269 A1 | 8/2006 | Glossop |
| 2006/0173291 A1 | 8/2006 | Glossop |
| 2006/0184016 A1 | 8/2006 | Glossop |
| 2006/0189867 A1 | 8/2006 | Revie et al. |
| 2006/0247511 A1 | 11/2006 | Anderson |
| 2006/0258933 A1 | 11/2006 | Elliss |
| 2006/0270976 A1 | 11/2006 | Savage et al. |
| 2007/0032723 A1 | 2/2007 | Glossop |
| 2007/0038058 A1 | 2/2007 | West et al. |
| 2007/0066887 A1 | 3/2007 | Mire et al. |
| 2007/0110289 A1 | 5/2007 | Fu et al. |
| 2007/0129629 A1 | 6/2007 | Beauregard et al. |
| 2007/0167714 A1 | 7/2007 | Kiraly et al. |
| 2007/0167744 A1 | 7/2007 | Beauregard et al. |
| 2007/0225559 A1 | 9/2007 | Clerc et al. |
| 2007/0232896 A1 | 10/2007 | Gilboa |
| 2007/0244355 A1 | 10/2007 | Shaw |
| 2007/0249896 A1 | 10/2007 | Goldfarb et al. |
| 2007/0276180 A1 | 11/2007 | Greenburg |
| 2008/0071142 A1 | 3/2008 | Gattani et al. |
| 2008/0071143 A1 | 3/2008 | Gattani et al. |
| 2008/0118135 A1 | 5/2008 | Averbuch |
| 2008/0125760 A1 | 5/2008 | Gilboa |
| 2008/0132757 A1 | 6/2008 | Tgavalekos |
| 2008/0140114 A1 | 6/2008 | Edwards et al. |
| 2008/0167639 A1 | 7/2008 | Gilboa |
| 2008/0221442 A1 | 9/2008 | Tolkowsky et al. |
| 2008/0247622 A1 | 10/2008 | Aylward et al. |
| 2008/0255416 A1 | 10/2008 | Gilboa |
| 2008/0262297 A1 | 10/2008 | Gilboa |
| 2008/0262342 A1 | 10/2008 | Averbruch |
| 2008/0269561 A1 | 10/2008 | Banik et al. |
| 2008/0287803 A1 | 11/2008 | Li et al. |
| 2009/0054908 A1 | 2/2009 | Zand et al. |
| 2009/0088600 A1 | 4/2009 | Meloul |
| 2009/0156895 A1 | 6/2009 | Higgins et al. |
| 2009/0156951 A1 | 6/2009 | Averbuch |
| 2009/0209817 A1 | 8/2009 | Averbuch |
| 2009/0227861 A1 | 9/2009 | Ganatra et al. |
| 2009/0240140 A1 | 9/2009 | Fitelzon |
| 2009/0240198 A1 | 9/2009 | Averbuch |
| 2009/0284255 A1 | 11/2009 | Zur |
| 2010/0036241 A1 | 2/2010 | Mayse et al. |
| 2010/0041949 A1 | 2/2010 | Tolkowsky |
| 2010/0160733 A1 | 6/2010 | Gilboa |
| 2012/0046521 A1 | 2/2012 | Hunter et al. |
| 2012/0059220 A1 | 3/2012 | Holsing et al. |
| 2012/0059248 A1 | 3/2012 | Holsing et al. |
| 2012/0065481 A1 | 3/2012 | Hunter et al. |
| 2012/0071753 A1 | 3/2012 | Hunter et al. |
| 2012/0123296 A1 | 5/2012 | Hashimshony et al. |

FOREIGN PATENT DOCUMENTS

| | | |
|---|---|---|
| DE | 19725137 C | 1/1999 |
| DE | 19829224 | 1/2000 |
| DE | 19829224 B | 1/2000 |
| DE | 19909816 | 5/2000 |
| DE | 199909816 | 5/2000 |
| DE | 10000937 | 8/2001 |
| DE | 10000937 B | 8/2001 |
| DE | 10136709 | 2/2003 |
| DE | 10136709 B | 2/2003 |
| DE | 10161160 | 6/2003 |
| DE | 102005010010 | 9/2005 |
| DE | 102004030836 | 1/2006 |
| DE | 102005026251 | 1/2006 |
| DE | 102005038394 | 3/2006 |
| DE | 102005050286 | 4/2006 |
| DE | 102004058122 | 7/2006 |
| EP | 0 501 993 B1 | 9/1992 |
| EP | 0501993 | 9/1992 |
| EP | 0 869 745 B1 | 10/1998 |
| EP | 0869745 | 10/1998 |
| EP | 900048 | 3/1999 |
| EP | 9000048 B1 | 3/1999 |
| EP | 0928600 | 7/1999 |
| EP | 977510 | 2/2000 |
| EP | 1 079 240 A | 2/2001 |
| EP | 1079240 | 2/2001 |
| EP | 1152706 | 11/2001 |
| EP | 1181897 | 2/2002 |
| EP | 1319368 | 6/2003 |
| EP | 1 374 792 A1 | 1/2004 |
| EP | 1 374 793 A1 | 1/2004 |
| EP | 1374792 | 1/2004 |
| EP | 1374793 | 1/2004 |
| EP | 1391181 | 2/2004 |
| EP | 1421913 | 5/2004 |
| EP | 1464285 | 10/2004 |
| EP | 1464285 B1 | 10/2004 |
| EP | 1 504 726 A1 | 2/2005 |
| EP | 1504713 | 2/2005 |
| EP | 1504726 | 2/2005 |
| EP | 1 519 140 A1 | 3/2005 |
| EP | 1519140 | 3/2005 |
| EP | 1 523 951 A2 | 4/2005 |
| EP | 1523951 | 4/2005 |
| EP | 1561423 | 8/2005 |
| EP | 1629774 | 3/2006 |
| EP | 1629789 | 3/2006 |
| EP | 2380550 | 10/2011 |
| FR | 2876273 | 4/2006 |
| JP | 2000023941 | 1/2000 |
| WO | 9424933 | 11/1994 |
| WO | 9501757 | 1/1995 |
| WO | 9501757 A1 | 1/1995 |
| WO | 9608209 | 3/1996 |
| WO | 9608209 A2 | 3/1996 |
| WO | 9610949 | 4/1996 |

(56) References Cited

FOREIGN PATENT DOCUMENTS

| | | |
|---|---|---|
| WO | 9626672 | 9/1996 |
| WO | 9729699 | 8/1997 |
| WO | 9729699 A1 | 8/1997 |
| WO | 9729709 | 8/1997 |
| WO | 9729709 A1 | 8/1997 |
| WO | 9836684 | 8/1998 |
| WO | 9916352 | 4/1999 |
| WO | 9927839 | 6/1999 |
| WO | 9943253 | 9/1999 |
| WO | 0016684 | 3/2000 |
| WO | 0028911 | 5/2000 |
| WO | 0047103 | 8/2000 |
| WO | 0049958 | 8/2000 |
| WO | 0057767 | 10/2000 |
| WO | 0069335 | 11/2000 |
| WO | 0101845 | 1/2001 |
| WO | 0137748 | 5/2001 |
| WO | 0162134 | 8/2001 |
| WO | 0164124 | 9/2001 |
| WO | 0176496 | 10/2001 |
| WO | 0176497 | 10/2001 |
| WO | 0187136 | 11/2001 |
| WO | 0193745 | 12/2001 |
| WO | 0200093 | 1/2002 |
| WO | 0200103 | 1/2002 |
| WO | 0219936 | 3/2002 |
| WO | 0222015 | 3/2002 |
| WO | 0224051 | 3/2002 |
| WO | 02056770 | 7/2002 |
| WO | 02064011 | 8/2002 |
| WO | 02082375 | 10/2002 |
| WO | 02098273 | 12/2002 |
| WO | 02098273 A2 | 12/2002 |
| WO | 2004046754 | 6/2004 |
| WO | 2004046754 A2 | 6/2004 |
| WO | 2004060157 | 7/2004 |
| WO | 2004062497 | 7/2004 |
| WO | 2004062497 A1 | 7/2004 |
| WO | 2005016166 | 2/2005 |
| WO | 2005070318 | 8/2005 |
| WO | 2005077293 | 10/2005 |
| WO | 2005101277 | 10/2005 |
| WO | 2005111942 | 11/2005 |
| WO | 2006002396 | 1/2006 |
| WO | 2006002396 A2 | 1/2006 |
| WO | 2006005021 | 1/2006 |
| WO | 2006005021 A2 | 1/2006 |
| WO | 2006027781 | 3/2006 |
| WO | 2006039009 | 4/2006 |
| WO | 2006051523 | 5/2006 |
| WO | 2006090141 | 8/2006 |
| WO | 2006090141 A1 | 8/2006 |
| WO | 2007002079 | 1/2007 |
| WO | 2007002079 A2 | 1/2007 |
| WO | 2007031314 | 3/2007 |
| WO | 2007031314 A2 | 3/2007 |
| WO | 2007033206 | 3/2007 |
| WO | 2007033206 A2 | 3/2007 |
| WO | 2007062051 | 5/2007 |
| WO | 2007062051 A2 | 5/2007 |
| WO | 2007084893 | 7/2007 |
| WO | 2007084893 A2 | 7/2007 |
| WO | 2009158578 | 12/2009 |
| WO | 2012024686 | 2/2012 |

OTHER PUBLICATIONS

Highlights from Presentation at 5th Joint Meeting of European Assn. for Cardio-Thoracic Surgery and European Society of Thoracic Surgeons "Evidence for Fleece-Bound Sealants in Cardiothoracic Surgery" Sep. 9-13, 2006.

Moore, E. et al., "Needle Aspiration Lung Biopsy: Re-evaluation of the Blood Patch Technique in an Equine Model", Radiology, vol. 196, No. 1, Jul. 1995.

FDA Approves Lung Sealant, May 31, 2000 [online], [retrieved on Oct. 17, 2008 from internet]; http://www.meds.com/archive/mol-cancer/2000/05/msg01329.html.

Patent Cooperation Treat, International Search Report and Written Opinion from PCT/US06/35548, mailed Aug. 20, 2007, 7 pages. Aug. 20, 2007.

European Patent Office, Extended Search Report issued for EP 11818898.6, mailed Dec. 20, 2013, 6 pages. Dec. 20, 2013.

Patent Cooperation Treaty, International Search Report issued for PCT/US2011/048669, mailed Apr. 9, 2012, 7 pages. Apr. 9, 2012.

New navigational aid could improve hip replacement outcomes, Medical Industry Today [online], Jul. 11, 1997, [retrieved on Jun. 24, 2003], retrieved from the Internet: <URL: http://www.lexis.com/research/retrieve?_m=d33d15f21cd1906aaea9118e9875d5cb&csvc=bl&c>.

* cited by examiner

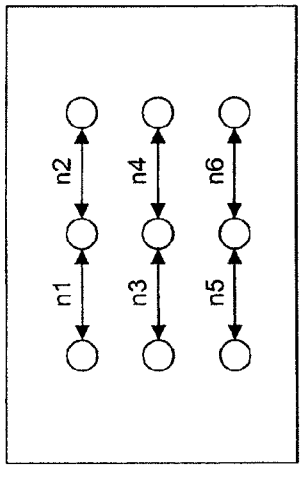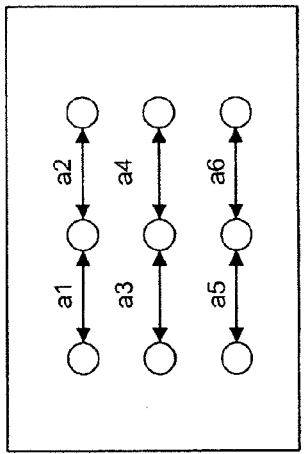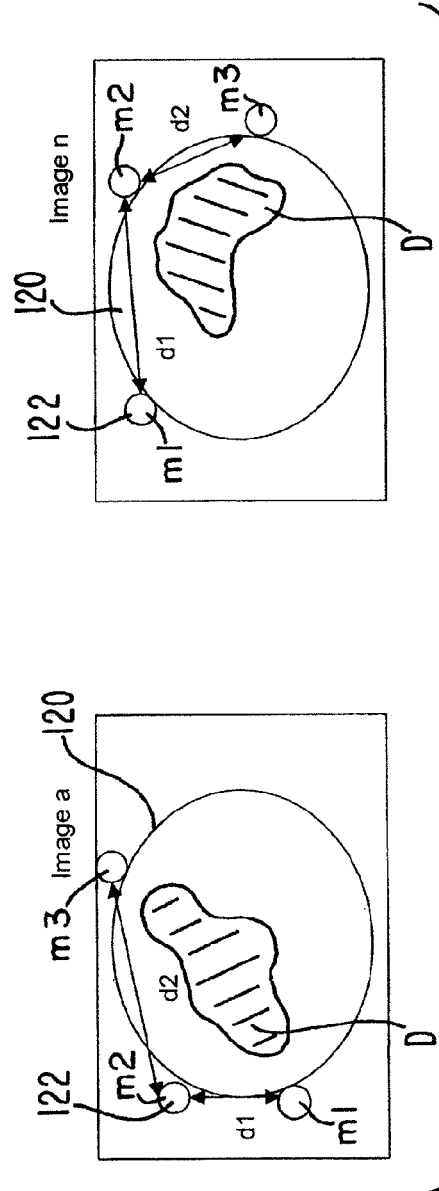
FIG. 4A
FIG. 4B

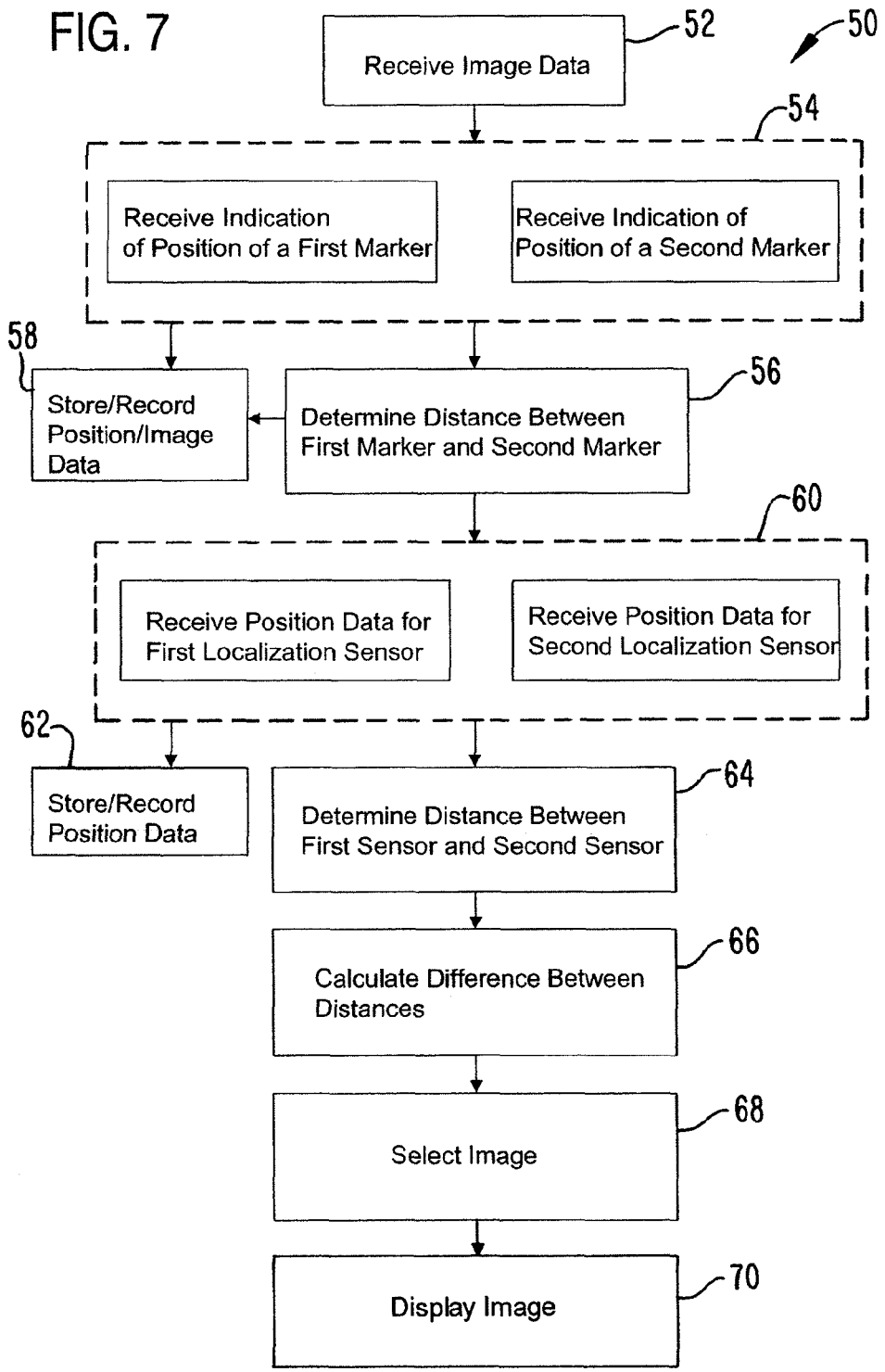

APPARATUS AND METHOD FOR IMAGE GUIDED ACCURACY VERIFICATION

CROSS-REFERENCE TO RELATED APPLICATIONS

This application is a continuation of U.S. patent application Ser. No. 11/224,028, filed on Sep. 13, 2005, now abandoned, which is incorporated herein by reference.

BACKGROUND

The invention relates generally to a medical device and particularly to an apparatus and method associated with image guided medical procedures.

Image guided surgery (IGS), also known as image guided intervention (IGI), enhances a physician's ability to locate instruments within anatomy during a medical procedure. IGS can include 2-dimensional (2-D) and 3-dimensional (3-D) applications.

Existing imaging modalities can capture the movement of dynamic anatomy. Such modalities include electrocardiogram (ECG)-gated or respiratory-gated magnetic resonance imaging (MRI) devices, ECG-gated or respiratory-gated computer tomography (CT) devices, and cinematography (CINE) fluoroscopy. The dynamic imaging modalities can capture the movement of anatomy over a periodic cycle of that movement by sampling the anatomy at several instants during its characteristic movement and then creating a set of image frames or volumes.

A need exists for an apparatus that can be used with such imaging devices to capture pre-procedural images of a targeted anatomical body and use those images intra-procedurally to help guide a physician to the correct location of the anatomical body during a medical procedure.

SUMMARY OF THE INVENTION

A method includes receiving during a first time interval image data associated with an image of a dynamic body. The image data includes an indication of a position of a first marker on a garment coupled to the dynamic body and a position of a second marker on the garment. The first marker is coupled to the garment at a first location. The second marker is coupled to the garment at a second location. A distance between the position of the first marker and the position of the second marker is determined. During a second time interval after the first time interval, data associated with a position of a first localization element coupled to the garment at the first location and data associated with a position of a second localization element coupled to the garment at the second location are received. A distance between the first localization element and the second localization element based on the data associated with the position of the first localization element and the position of the second localization element is determined. A difference is calculated between the distance between the first marker and the second marker during the first time interval and the distance between the first localization element and the second localization element during the second time interval.

BRIEF DESCRIPTION OF THE DRAWINGS

The present invention is described with reference to the accompanying drawings.

FIG. 4A is a schematic illustrating vector distances from a localization device according to an embodiment of the invention.

FIG. 4B is a schematic illustrating vector distances from image data according to an embodiment of the invention.

FIG. 7 is a flowchart illustrating a method according to an embodiment of the invention.

DETAILED DESCRIPTION

Figure 1:
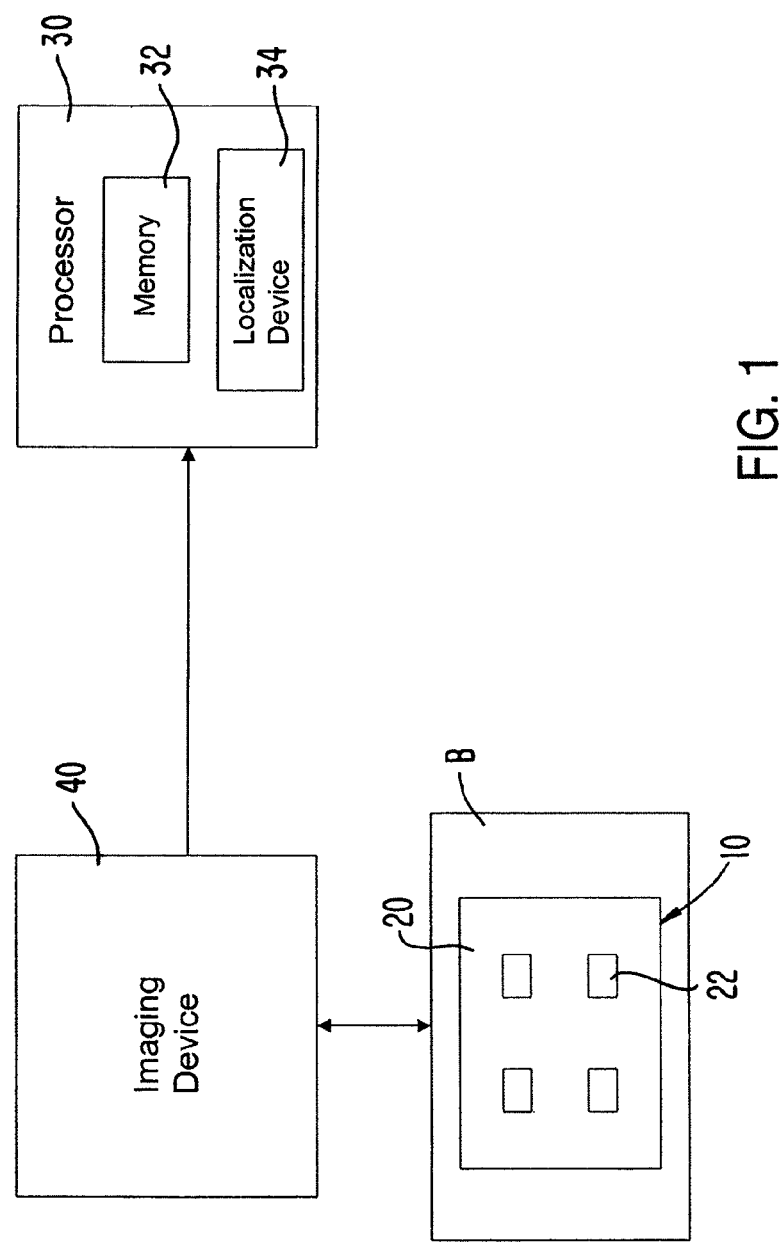
FIG. 1 is a schematic illustration of various devices used with a method according to an embodiment of the invention.

An apparatus according to an embodiment of the invention includes a garment and two or more markers coupled to the garment. The apparatus can also include two or more localization elements coupled to the garment proximate the markers. The apparatus is configured to be coupled to a dynamic body, such as selected dynamic anatomy of a patient. Dynamic anatomy can be, for example, any anatomy that moves during its normal function (e.g., the heart, lungs, kidneys, liver and blood vessels). A processor, such as a computer, is configured to receive image data associated with the dynamic body taken during a pre-surgical or pre-procedural first time interval. The image data can include an indication of a position of each of the markers for multiple instants in time during the first time interval. The processor can also receive position data associated with the localization elements during a second time interval in which a surgical procedure or other medical procedure is being performed. The processor can use the position data received from the localization elements to determine a distance between the elements for a given instant in time during the second time interval. The processor can also use the image data to determine the distance between the markers for a given instant in time during the first time interval. The processor can then find a match between an image where the distance between the markers at a given instant in time during the first time interval is the same as the distance between the elements associated with those markers at a given instant in time during the medical procedure, or second time interval.

A physician or other healthcare professional can use the images selected by the processor during a medical procedure performed during the second time interval. For example, when a medical procedure is performed on a targeted anatomy of a patient, such as a heart, the physician may not be able to utilize an imaging device during the medical procedure to guide him to the targeted area within the patient. A garment according to an embodiment of the invention can be positioned or coupled to the patient proximate the targeted anatomy prior to the medical procedure, and pre-procedural images can be taken of the targeted area during a first time interval. Markers or fiducials coupled to the garment can be viewed with the image data, which can include an indication of the position of the markers during a given path of motion of the targeted anatomy (e.g., the heart) during the first time interval. Such motion can be due, for example, to inspiration (i.e., inhaling) and expiration (i.e., exhaling) of the patient, or due to the heart beating. During a medical procedure, performed during a second time interval, such as a procedure on a heart, the processor receives data from the localization elements associated with a position of the elements at a given instant in time during the medical procedure (or second time interval). The distance between selected pairs of markers can be determined from the image data and the distance between corresponding selected pairs of localization elements can be determined based on the element data for given instants in time.

Because the localization elements are coupled to the garment proximate the location of the markers, the distance between a selected pair of elements can be used to determine an intra-procedural distance between the pair of corresponding markers to which the localization elements are coupled. An image from the pre-procedural image data taken during the first time interval can then be selected where the distance between the pair of selected markers in that image corresponds with or closely approximates the same distance determined using the localization elements at a given instant in time during the second time interval. This process can be done continuously during the medical procedure, producing simulated real-time, intra-procedural images illustrating the orientation and shape of the targeted anatomy as a catheter or similar structure is navigated to the targeted anatomy. Thus, during the medical procedure, the physician can view selected image(s) of the targeted anatomy that correspond to and simulate real-time movement of the anatomy. In addition, during a medical procedure being performed during the second time interval, such as navigating a catheter to a targeted anatomy, the location(s) of an electromagnetic coil coupled to the catheter during the second time interval can be superimposed on an image of a catheter. The superimposed image(s) of the catheter can then be superimposed on the selected image(s) from the first time interval, providing simulated real time images of the catheter location relative to the targeted anatomy. This process and other related methods are described in U.S. Pat. No. 7,398,116, entitled Methods, Apparatuses, and Systems Useful in Conducting Image Guided Interventions, filed Aug. 26, 2003.

Figure 2:
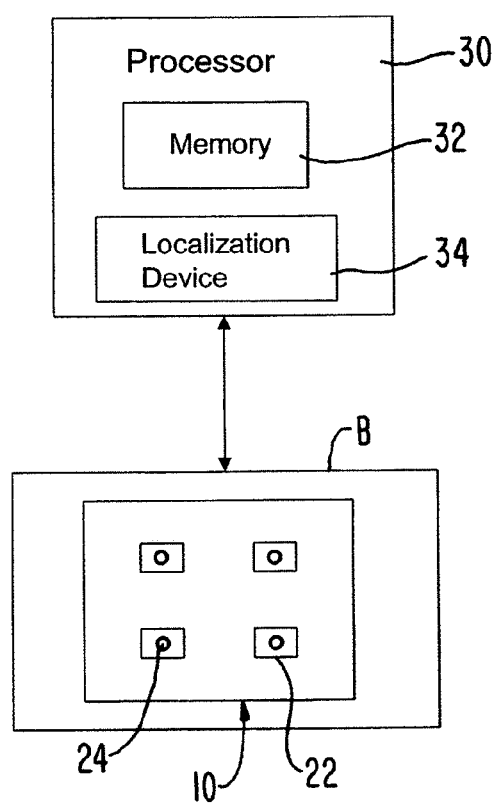
FIG. 2 is a schematic illustration of various devices used with a method according to an embodiment of the invention.

FIGS. 1 and 2 are schematic illustrations of devices that can be used to perform various procedures described herein. As shown in FIG. 1, an apparatus 10 includes a garment 20. The garment 20 can be coupled to a dynamic body B. The dynamic body B can be, for example, a selected dynamic portion of the anatomy of a patient. The garment 20 can be a variety of different shapes and sizes. For example, in one embodiment the garment 20 is a tubular or sleeve configuration (see FIG. 5) and can fit, for example, around the torso of a patient, or around the upper chest surrounding, for example, the patient's heart. The garment 20 can be a continuous tubular configuration or a partial tubular configuration. For example, the garment 20 may be substantially planar prior to coupling to the dynamic body and then wrapped around the dynamic body and coupled to the dynamic body using an attachment, such as straps, hook and pile fastener, snaps, or any other suitable coupling method. In the case of a continuous tubular shape, the garment 20 may be held in position on the dynamic body through friction fit, or due to the garment being stretchable such that it conforms to the dynamic body. In another embodiment, the garment 20 is substantially planar, such as in the form of a patch that can be disposed at a variety of locations on a patient's body. Such a garment 20 can be coupled to the dynamic body with adhesive, straps, hook and pile, snaps, or any other suitable coupling method.

In some embodiments, the garment 20 is configured as a shirt to be worn by a patient. In some embodiments, the garment 20 is configured to be worn similar to a pair of pants. In still other embodiments, a garment is configured as an undergarment to be worn by a patient. For example, a garment can be configured as an undergarment to be worn on the upper torso of the patient (e.g., a brassiere). These configurations may allow, for example, placement of markers at varying angles relative to the targeted anatomy of the patient.

The garment 20 can be constructed with a variety of different materials, such as fabric, plastic, and rubber and can be flexible, stretchable and/or rigid. In some embodiments, the garment 20 is configured to constrict movement of the dynamic body B. For example, the garment 20 can be constructed in a tubular configuration with a stretchable material that when coupled to the patient's body, constricts at least a portion of the patient's movement through inhaling and exhaling or movement caused by the heart beating.

Two or more markers or fiducials 22 are coupled to the garment 20 at selected locations as shown in FIG. 1. The markers 22 are constructed of a material that can be viewed on an image, such as an X-ray. The markers 22 can be, for example, radiopaque, and can be coupled to the garment 20 using any known methods of coupling such devices. FIGS. 1 and 2 illustrate the apparatus 10 having four markers 22, but any number of two or more markers can be used.

An imaging device 40 can be used to take images of the dynamic body B while the garment 20 is coupled to the dynamic body B, pre-procedurally during a first time interval. As stated above, the markers 22 are visible on the images and can provide an indication of a position of each of the markers 22 during the first time interval. The position of the markers 22 at given instants in time through a path of motion of the dynamic body B can be illustrated with the images. The imaging device 40 can be, for example, a computed tomography (CT) device (e.g., respiratory-gated CT device, ECG-gated CT device), a magnetic resonance imaging (MRI) device (e.g., respiratory-gated MRI device, ECG-gated MRI device), an X-ray device, or any other suitable medical imaging device. In one embodiment, the imaging device 40 is a computed tomography-positron emission tomography device that produces a fused computed tomography-positron emission tomography image dataset. The imaging device 40 can be in communication with a processor 30 and send, transfer, copy and/or provide image data taken during the first time interval associated with the dynamic body B to the processor 30.

The processor 30 includes a processor-readable medium storing code representing instructions to cause the processor 30 to perform a process. The processor 30 can be, for example, a commercially available personal computer, or a less complex computing or processing device that is dedicated to performing one or more specific tasks. For example, the processor 30 can be a terminal dedicated to providing an interactive graphical user interface (GUI). The processor 30, according to one or more embodiments of the invention, can be a commercially available microprocessor. Alternatively, the processor 30 can be an application-specific integrated circuit (ASIC) or a combination of ASICs, which are designed to achieve one or more specific functions, or enable one or more specific devices or applications. In yet another embodiment, the processor 30 can be an analog or digital circuit, or a combination of multiple circuits.

The processor 30 can include a memory component 32. The memory component 32 can include one or more types of memory. For example, the memory component 32 can include a read only memory (ROM) component and a random access memory (RAM) component. The memory component can also include other types of memory that are suitable for storing data in a form retrievable by the processor 30. For example, electronically programmable read only memory (EPROM), erasable electronically programmable read only memory (EEPROM), flash memory, as well as other suitable forms of memory can be included within the memory component. The processor 30 can also include a variety of other components, such as for example, co-processors, graphic processors, etc., depending upon the desired functionality of the code.

The processor 30 can store data in the memory component 32 or retrieve data previously stored in the memory component 32. The components of the processor 30 can communicate with devices external to the processor 30 by way of an input/output (I/O) component (not shown). According to one or more embodiments of the invention, the I/O component can include a variety of suitable communication interfaces. For example, the I/O component can include, for example, wired connections, such as standard serial ports, parallel ports, universal serial bus (USB) ports, S-video ports, local area network (LAN) ports, small computer system interface (SCCI) ports, and so forth. Additionally, the I/O component can include, for example, wireless connections, such as infrared ports, optical ports, Bluetooth® wireless ports, wireless LAN ports, or the like.

The processor 30 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

As stated above, the processor 30 can receive image data from the imaging device 40. The processor 30 can identify the position of selected markers 22 within the image data or voxel space using various segmentation techniques, such as Hounsfield unit thresholding, convolution, connected component, or other combinatory image processing and segmentation techniques. The processor 30 can determine a distance and direction between the position of any two markers 22 during multiple instants in time during the first time interval, and store the image data, as well as the position and distance data, within the memory component 32. Multiple images can be produced providing a visual image at multiple instants in time through the path of motion of the dynamic body. The processor 30 can also include a receiving device or localization device 34, which is described in more detail below.

As shown in FIG. 2, two or more localization elements 24 are coupled to the garment 20 proximate the locations of the markers 22 for use during a medical procedure to be performed during a second time interval. The localization elements 24 can be, for example, electromagnetic coils, infrared light emitting diodes, and/or optical passive reflective markers. The markers 22 can include plastic or non-ferrous fixtures or dovetails or other suitable connectors used to couple the localization elements 24 to the markers 22. A medical procedure can then be performed with the garment 20 coupled to the dynamic body B at the same location as during the first time interval when the pre-procedural images were taken. During the medical procedure, the localization elements 24 are in communication or coupled to the localization device 34 included within processor 30. The localization device 34 can be, for example, an analog to digital converter that measures voltages induced onto localization coils in the field; creates a digital voltage reading; and maps that voltage reading to a metric positional measurement based on a characterized volume of voltages to millimeters from a fixed field emitter. Position data associated with the elements 24 can be transmitted or sent to the localization device 34 continuously during the medical procedure during the second time interval. Thus, the position of the localization elements 24 can be captured at given instants in time during the second time interval. Because the localization elements 24 are coupled to the garment 20 proximate the markers 22, the localization device 34 can use the position data of the elements 24 to deduce coordinates or positions associated with the markers 22 intra-procedurally during the second time interval. The distance between one or more selected pairs of localization elements 24 (and corresponding markers 22) can then be determined and various algorithms can be used to analyze and compare the distance between selected elements 24 at given instants in time, to the distances between and orientation among corresponding markers 22 observed in the pre-operative images.

An image can then be selected from the pre-operative images taken during the first time interval that indicates a distance between corresponding markers 22 at a given instant in time, that most closely approximates or matches the distance between the selected elements 24. The process of comparing the distances is described in more detail below. Thus, the apparatus 10 and processor 30 can be used to provide images corresponding to the actual movement of the targeted anatomy during the medical procedure being performed during the second time interval. The images illustrate the orientation and shape of the targeted anatomy during a path of motion of the anatomy, for example, during inhaling and exhaling.

Figure 3:
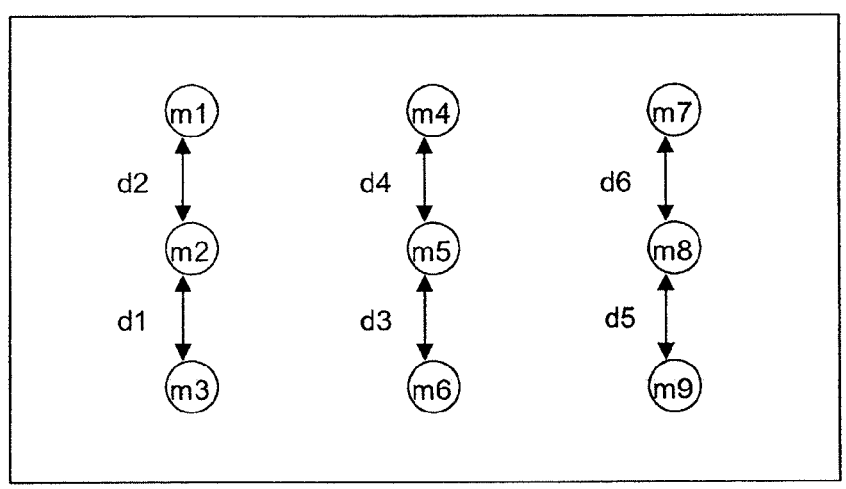
FIG. 3 is a schematic illustrating vector distances on an apparatus according to an embodiment of the invention.

FIG. 3 illustrates an example set of distances or vectors d1 through d6 between a set of markers 122, labeled m1 through m9 that are disposed at spaced locations on a garment 120. As described above, pre-procedure images can be taken of a dynamic body for which the garment 120 is to be coupled during a first time interval. The distances between the markers can be determined for multiple instants in time through the path of motion of the dynamic body. Then, during a medical procedure, performed during a second time interval, localization elements (not shown in FIG. 3) coupled proximate to the location of markers 122 can provide position data for the elements to a localization device (not shown in FIG. 3). The localization device can use the position data to determine distances or vectors between the elements for multiple instants in time during the medical procedure or second time interval.

FIG. 4A shows an example of distance or vector data from the localization device. Vectors a1 through a6 represent distance data for one instant in time and vectors n1 through n6 for another instant in time, during a time interval from a to n. As previously described, the vector data can be used to select an image from the pre-procedural images that includes distances between the markers m1 through m9 that correspond to or closely approximate the distances a1 through a6 for time a, for example, between the localization elements. The same process can be performed for the vectors n1 through n6 captured during time n.

One method of selecting the appropriate image from the pre-procedural images is to execute an algorithm that can sum all of the distances a1 through a6 and then search for and match this sum to an image containing a sum of all of the distances d1 through d6 obtained pre-procedurally from the image data that is equal to the sum of the distances a1 through a6. When the difference between these sums is equal to zero, the relative position and orientation of the anatomy or dynamic body D during the medical procedure will substantially match the position and orientation of the anatomy in the particular image. The image associated with distances d1 through d6 that match or closely approximate the distances a1 through a6 can then be selected and displayed. For example, FIG. 4B illustrates examples of pre-procedural images, Image a and Image n, of a dynamic body D that correspond to the distances a1 through a6 and n1 through n6, respectively. An example of an algorithm for determining a match is as follows:

Does $\Sigma a_i = \Sigma_i$ (i=1 to 6 in this example) OR

Does $\Sigma (a_i - d_i) = 0$ (i=1 to 6 in this example).

If yes to either of these, then the image is a match to the vector or distance data obtained during the medical procedure.

Figure 5:
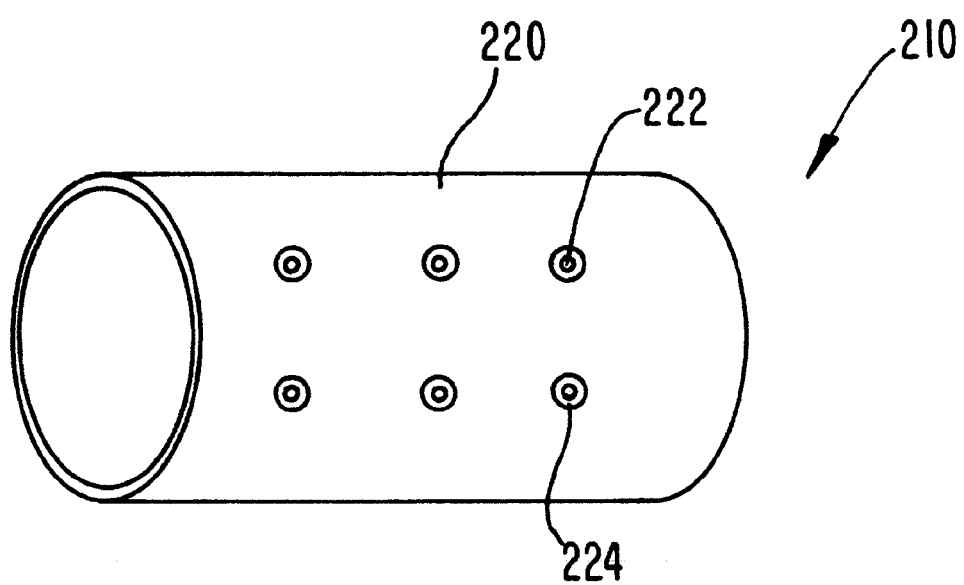
FIG. 5 is a front perspective view of an apparatus according to an embodiment of the invention.

FIG. 5 illustrates an apparatus 210 according to an embodiment of the invention. The apparatus 210 includes a tubular shaped garment 220 that can be constructed with a flexible and/or stretchable material. The garment 220 can be positioned over a portion of a patient's body, such as around the upper or lower torso of the patient. The stretchability of the garment 220 allows the garment 220 to at least partially constrict some of the movement of the portion of the body for which it is coupled. The apparatus 210 further includes multiple markers or fiducials 222 coupled to the garment 220 at spaced locations. A plurality of localization elements 224 are removably coupled proximate to the locations of markers 222, such that during a first time interval as described above, images can be taken without the elements 224 being coupled to the garment 220. The localization elements need not be removably coupled. For example, the elements can be fixedly coupled to the garment. In addition, the elements can be coupled to the garment during the pre-procedure imaging.

Figure 6:
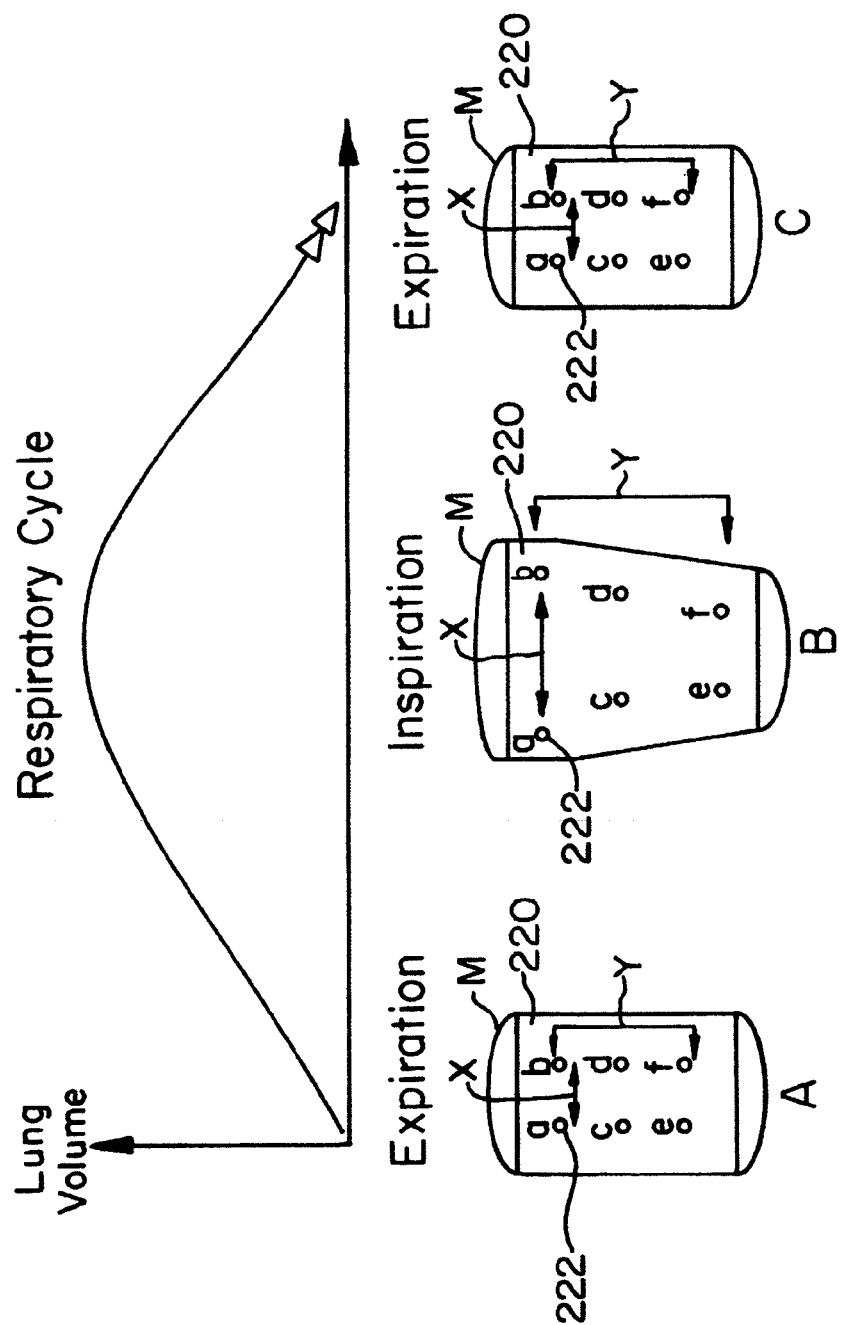
FIG. 6 is a graphical representation illustrating the function of an apparatus according to an embodiment of the invention.

FIG. 6 is a graphical illustration indicating how the apparatus 210 (shown without localization elements 224) can move and change orientation and shape during movement of a dynamic body, such as a mammalian body M. The graph is one example of how the lung volume can change during inhalation (inspiration) and exhalation (expiration) of the mammalian body M. The corresponding changes in shape and orientation of the apparatus 210 during inhalation and exhalation are also illustrated. The six markers 222 shown in FIG. 5 are labeled a, b, c, d, e, and f. As described above, images of the apparatus 110 can be taken during a first time interval. The images can include an indication of relative position of each of the markers 222, that is the markers 222 are visible in the images, and the position of each marker 222 can then be observed over a period of time. A distance between any two markers 222 can then be determined for any given instant of time during the first time interval. For example, a distance X between markers a and b is illustrated, and a distance Y between markers b and f is illustrated. These distances can be determined for any given instant in time during the first time interval from an associated image that illustrates the position and orientation of the markers 222. As illustrated, during expiration of the mammalian body M at times indicated as A and C, the distance X is smaller than during inspiration of the mammalian body M, at the time indicated as B. Likewise, the distance Y is greater during inspiration than during expiration. The distance between any pair of markers 222 can be determined and used in the processes described herein. Thus, the above embodiments are merely examples of possible pair selections. For example, a distance between a position of marker e and a position of marker b may be determined. In addition, multiple pairs or only one pair may be selected for a given procedure.

FIG. 7 is a flowchart illustrating a method according to an embodiment of the invention. A method 50 includes at step 52 receiving image data during a pre-procedural or first time interval. As discussed above, images are taken of a dynamic body using an appropriate imaging modality (e.g., CT Scan, MRI, etc.). The image data is associated with one or more images taken of a garment (as described herein) coupled to a dynamic body, where the garment includes two or more markers coupled thereto. In other words, the image data of the dynamic body is correlated with image data related to the garment. The one or more images can be taken using a variety of different imaging modalities as described previously. The image data can include an indication of a position of a first marker and an indication of a position of a second marker, as illustrated at step 54. The image data can include position data for multiple positions of the markers during a range or path of motion of the dynamic body over a selected time interval. As described above, the image data can include position data associated with multiple markers, however, only two are described here for simplicity. A distance between the position of the first marker and the position of the second marker can be determined for multiple instants in time during the first time interval, at step 56. As also described above, the determination can include determining the distance based on the observable distance between the markers on a given image. The image data, including all of the images received during the first time interval, the position, and the distance data can be stored in a memory and/or recorded at step 58.

Then at step 60, during a second time interval, while performing a medical procedure on the patient with the garment positioned on the patient at substantially the same location, position data can be received for a first localization element and a second localization element. The localization elements can be coupled to the garment proximate the locations of the markers, such that the position data associated with the elements can be used to determine the relative position of the markers in real-time during the medical procedure. The position data of the elements can be stored and/or recorded at step 62.

A distance between the first and second localization elements can be determined at step 64. Although only two localization elements are described, as with the markers, position data associated with more than two localization elements can be received and the distances between the additional elements can be determined.

The next step is to determine which image from the one or more images taken during the first time interval represents the relative position and/or orientation of the dynamic body at a given instant in time during the second time interval or during the medical procedure. To determine this, at step 66, the distance between the positions of the first and second localization elements at a given instant in time during the second time interval are compared to the distance(s) determined in step 56 between the positions of the first and second markers obtained with the image data during the first time interval.

An image can be selected from the first time interval that best represents the same position and orientation of the dynamic body at a given instant in time during the medical procedure. To do this, the difference between the distance between a given pair of localization elements during the second time interval is used to select the image that contains the same distance between the same given pair of markers from the image data received during the first time interval. This can be accomplished, for example, by executing an algorithm to perform the calculations. When there are multiple pairs of markers and localization elements, the algorithm can sum the distances between all of the selected pairs of elements for a given instant in time during the second time interval and sum the distances between all of the associated selected pairs of markers for each instant in time during the first time interval when the pre-procedural image data was received.

When an image is found that provides the sum of distances for the selected pairs of markers that is substantially the same as the sum of the distances between the localization elements during the second time interval, then that image is selected at step 68. The selected image can then be displayed at step 70. The physician can then observe the image during the medical procedure on a targeted portion of the dynamic body. Thus, during the medical procedure, the above process can be continuously executed such that multiple images are displayed and images corresponding to real-time positions of the dynamic body can be viewed.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the garment, markers and localization elements can be constructed from any suitable material, and can be a variety of different shapes and sizes, not necessarily specifically illustrated, while still remaining within the scope of the invention.

What is claimed is:

1. An apparatus, comprising:
a first radiopaque marker coupled to a device at a first location, a second radiopaque marker coupled to the device at a second location, wherein the first and second markers change in orientation relative to each other during a path of motion of a dynamic body;
a first element coupled to the device proximate the location of the first marker; and a second element coupled to the device proximate the location of the second marker;
the first element and the second element each being coupled to a processor and configured to simultaneously send to the processor position data associated with a plurality of positions in three-dimensional space of the first element and position data associated with a plurality of positions in three-dimensional space of the second element during the path of motion of the dynamic body;
wherein the processor determines a vector distance between the position of the first element and the position of the second element based on the position data for each instant of time for a plurality of instants of time during the motion of the dynamic body.

2. The apparatus of claim 1 wherein the device is a garment having a continuous tubular configuration, a partial tubular configuration, or a substantially planar configuration.

3. The apparatus of claim 1 wherein the dynamic body is the heart of a patient and the path of motion of the dynamic body correlates with the heart beating.

4. The apparatus of claim 1 wherein the dynamic body is a lung of a patient and the path of motion of the dynamic body correlates with at least one of inspiration and expiration.

5. The apparatus of claim 1 wherein the processor determines the vector distance using a segmentation technique selected from Houndsfield unit thresholding, convolution, connected component, combinatory image processing, and combinations thereof.

6. The apparatus of claim 1 wherein the first element and the second element are each one of electromagnetic coils, optical infrared light emitting diodes, optical passive reflective markers, or voltage induced coils.

7. A method, comprising:
receiving, by a processor, during a first time interval, image data associated with a path of motion of a dynamic body, the image data including a plurality of images each indicating a position of a first radiopaque marker on a device coupled to the dynamic body proximate to a targeted anatomy and a position of a second radiopaque marker on the device coupled to the dynamic body for an instant in time throughout the path of motion of the dynamic body, the first radiopaque marker being physically coupled to the device at a first location, the second radiopaque marker being physically coupled to the device at a second location, wherein the first and second radiopaque markers change in orientation relative to each other during the first time interval, and wherein the first and second radiopaque markers are visible in the plurality of images;
determining, by a processor, a vector distance between the position of the first radiopaque marker and the position of the second radiopaque marker in three-dimensional space based on the position of the first radiopaque marker and the position of the second radiopaque marker for each instant of time;
receiving, by a processor, during a medical procedure performed during a second time interval after the first time interval, position data sent to the processor from a first localization element and a second localization element, the position data associated with a position in three-dimensional space of the first localization element physically coupled to the device at the first location and the position data associated with a position in three-dimensional space of the second localization element physically coupled to the device at the second location, and wherein the first and second localization elements change in orientation relative to each other during the second time interval;
determining, by a processor, a vector distance between the position of the first localization element and the position of the second localization element based on the data associated with the position of the first localization element and the position of the second localization element; and
generating, by a processor, simulated, real-time images of the orientation and shape of the targeted anatomy during the medical procedure performed during the second time interval, the generation comprising continuously selecting an image from the plurality of images received during the first time interval and comparing the vector distance between the first radiopaque marker and the second radiopaque marker determined during the first time interval with the vector distance between the first localization element and the second localization element calculated at a given instant of time during the second time interval.

8. The method of claim 7 wherein the medical procedure comprises navigating a navigatable catheter to the targeted anatomy.

9. The method of claim 8 wherein the generation further comprises superimposing, by a processor, the location of an electromagnetic coil coupled to the navigatable catheter on an image of the navigatable catheter to form a superimposed catheter image, and further superimposing, by a processor, the superimposed catheter image on the selected image from the plurality of images received during the first time interval.

10. The method of claim 7 wherein the device is a garment having a continuous tubular configuration, a partial tubular configuration, or a substantially planar configuration.

11. The method of claim 7 wherein the dynamic body is the heart of a patient and the path of motion of the dynamic body correlates with the heart beating.

12. The method of claim 7 wherein the dynamic body is a lung of a patient and the path of motion of the dynamic body correlates with at least one of inspiration and expiration.

13. The method of claim 7 wherein the vector distance is determined using a segmentation technique selected from Houndsfield unit thresholding, convolution, connected component, combinatory image processing, and combinations thereof.

14. The method of claim 7 wherein the receiving image data includes receiving, by a processor, image data from a computed tomography device.

15. The method of claim 7 wherein the receiving image data includes receiving, by a processor, image data from a computed tomography-positron emission tomography device that produces a fused computed tomography-positron emission tomography image dataset.

16. The method of claim 7 wherein the receiving image data includes receiving, by a processor, image data from a magnetic resonance imaging device.

17. The method of claim 7 further comprising:
receiving, by a processor, the data associated with a position of the first localization element and the data associated with a position of the second localization element continuously during the second time interval and recording, by a processor, the data associated with a position of the first localization element and the data associated with a position of the second localization element continuously during the second time interval.

18. A non-transitory processor-readable medium storing code representing instructions to cause a processor to perform a process, the code comprising code to:
receive, during a first time interval, image data associated with a path of motion in three-dimensional space of a dynamic body, the image data including a plurality of images taken using an imaging device;
receive, during the first time interval, position data based on the image data received, the position data indicating a position in three-dimensional space of a first radiopaque marker on a device coupled to the dynamic body proximate to a targeted anatomy and a position in three-dimensional space of a second radiopaque marker on the device coupled to the dynamic body for a plurality of instants of time during the first time interval and throughout the path of motion of the dynamic body, the first radiopaque marker being physically coupled to the device at a first location, the second radiopaque marker being physically coupled to the device at a second location, wherein the first and second radiopaque markers change in orientation relative to each other during the first time interval, and wherein the first and second radiopaque markers are visible in the image data;
determine a vector distance between the position of the first radiopaque marker and the position of the second radiopaque marker in three-dimensional space based on the position data for each instant of time from the plurality of instants of time during the first interval;
receive, during a medical procedure performed during a second time interval after the first time interval, position data sent to the processor from a first localization element and a second localization element, the position data associated with a position in three-dimensional space of the first localization element physically coupled to the device at the first location and the position data associated with a position in three-dimensional space of the second localization element physically coupled to the device at the second location, and wherein the first and second localization elements change in orientation relative to each other during the second time interval;
determine a vector distance between the position of the first localization element and the position of the second localization element based on the data associated with the position of the first localization element and the position of the second localization element; and
generate simulated, real-time images of the orientation and shape of the targeted anatomy during the medical procedure performed during the second time interval, the generation comprising continuously selecting an image from the plurality of images received during the first time interval and comparing the vector distance between the first radiopaque marker and the second radiopaque marker determined during the first time interval with the vector distance between the first localization element and the second localization element calculated at a given instant of time during the second time interval.

19. The non-transitory processor-readable medium of claim 18 wherein the comparing includes executing an algorithm configured to compare the determined vector distances associated with the first radiopaque marker and the second radiopaque marker to the vector distance associated with the first localization element and the second localization element.

20. The non-transitory processor-readable medium of claim 18 wherein the device is a garment having a continuous tubular configuration, a partial tubular configuration, or a substantially planar configuration.

21. The non-transitory processor-readable medium of claim 18 wherein the dynamic body is the heart of a patient and the path of motion of the dynamic body correlates with the heart beating.

22. The non-transitory processor-readable medium of claim 18 wherein the dynamic body is a lung of a patient and the path of motion of the dynamic body correlates with at least one of inspiration and expiration.

23. The non-transitory processor-readable medium of claim 18 wherein the vector distance is determined using a segmentation technique selected from Houndsfield unit thresholding, convolution, connected component, combinatory image processing, and combinations thereof.

24. The non-transitory processor-readable medium of claim 18 wherein the receiving image data includes receiving image data from a computed tomography device.

25. The non-transitory processor-readable medium of claim 18 wherein the receiving image data includes receiving image data from a computed tomography-positron emission tomography device that produces a fused computed tomography-positron emission tomography image dataset.

26. The non-transitory processor-readable medium of claim 18 wherein the receiving image data includes receiving image data from a magnetic resonance imaging device.

* * * * *